United States Patent [19]
Cohen

[11] Patent Number: 5,837,253
[45] Date of Patent: Nov. 17, 1998

[54] PREPARATION AND USE OF INULA EXTRACTS AS A FUNGICIDE FOR THE CONTROL OF PLANT DISEASES

[75] Inventor: Yigal Cohen, Kiryat Ono, Israel

[73] Assignee: Agrogene Ltd., Israel

[21] Appl. No.: 739,699

[22] Filed: Oct. 29, 1996

Related U.S. Application Data

[63] Continuation-in-part of Ser. No. 690,423, Jul. 26, 1996.
[51] Int. Cl.$^6$ .................................................. A61K 35/78
[52] U.S. Cl. ............................................... 424/195.1
[58] Field of Search ........................................ 424/195.1

[56] References Cited

U.S. PATENT DOCUMENTS

| | | | |
|---|---|---|---|
| 4,254,112 | 3/1981 | Debat et al. | 424/195.1 |
| 4,358,286 | 11/1982 | Grollier et al. | 8/405 |
| 4,460,488 | 7/1984 | Grollier et al. | 252/89.1 |
| 5,176,913 | 1/1993 | Honerlagen et al. | 424/195.1 |
| 5,178,865 | 1/1993 | Ho et al. | 424/195.1 |

FOREIGN PATENT DOCUMENTS 083317   4/1984   Romania.

OTHER PUBLICATIONS

Quasem, J. R., et al., "Antifungal Activity of Clammy Inula (*Inula Viscosa*) on *Heminthosporium Sativum* and *Fusarium Axysporum* F. Sp. Lycopersici", Phytopath. Medit., vol. 34, pp. 7–14, 1995.

Yegen, O., et al., Investigations on the Fungitoxicity of Extracts of Six Selected Plants from Turkey Against Phytopathogenic Fungi:, J. Plant Dis. & Prot., 99(4), pp. 349–459, 1992.

Shao, Y., et a., "Kaurane Glycosides from *Inula Britannica*", Phytochem., vol. 42, No. 3, pp. 783–786, 1996.

Ziv O., "Using Extracts of *Inula Viscosa* for Controlling Plant Diseases on Fresh and Dry Postharvest Pfroducts", Phytoparasitica, vol. 24(2) p. 154, 1996.

Grande, M. et al., "Triterpenoids from *Ditrichia Viscosa*", Phytochem., vol. 31, No. 5, pp. 1826–1828, 1992.

Gulacti, T. et al., "Structurally related guaianolides from *Inula Thapsoidies*", Phytochem., vol. 40, No. 4, pp. 1717–1722, 1995.

Sanz, J., et al., "oxygenated nerolidol esters and eudesmane acids from *Inula Viscosa*", Phytochem., vol. 30. No. 11, pp. 3653–3655, 1991.

Gulacti, T., et al., "Cytotoxic and antibacterial sesquiterpenes from *Inula Graveolens*", Phytochem., vol. 33, No. 2, pp. 407–410, 1993.

*Primary Examiner*—Chhaya D. Sayala
*Attorney, Agent, or Firm*—Gifford, Krass, Groh, Sprinkle, Patmore, Anderson & Citkowski, P.C.

[57] ABSTRACT

Rapid, convenient and inexpensive methods for preparing fungicidal suspensions from Inula are described. Methods for controlling fungal disease in crops by using these suspensions are also given.

16 Claims, No Drawings

PREPARATION AND USE OF INULA EXTRACTS AS A FUNGICIDE FOR THE CONTROL OF PLANT DISEASES

This is a continuation-in-part of U.S. patent application Ser. No. 08/690,423, filed Jul. 26, 1996.

FIELD AND BACKGROUND OF THE INVENTION

The present invention relates to fungicides and, more particularly, to fungicidal plant extracts and suspensions from Inula species, which are effective against fungal plant infections.

Extracts of plants which are members of the Inula species are effective against infections of plants caused by a variety of fungi. These extracts are prepared by dipping freshly cut Inula shoots in an organic solvent, or agitating freshly cut or dried Inula shoots in an organic solvent, blowing off the solvent so that a paste is formed, and then dissolving this paste in an organic solvent or in water with an additive. Alternatively, suspensions of Inula can be prepared by grinding dried Inula shoots to a fine powder, adding an emulsifier, and then suspending the mixture in water. In both cases, the resultant preparation is then applied to plants, resulting in the control of a wide variety of fungal diseases. Extracts and suspensions of Inula plants are effective at low concentrations, in the fractions of a single percent of extract, so that dilute concentrations have excellent fungal-control properties.

The plants which are the basis of these fungicidal extracts and suspensions are *Inula viscosa* and *Inula graveolens* (Family Compositae), perennial weeds widespread in the Mediterranean basin.

Methods of preparing aqueous extracts from various parts of the Inula plant are well known in the literature. By contrast, the present invention uses organic solvents. Furthermore, as shown below in Examples 2, 10 and 11, aqueous extracts are not as fungicidally effective as extracts prepared according to the present invention.

Methods have also been described which use organic solvents to extract Inula plants, but these can be clearly distinguished from the present invention. Two of these methods involve contacting the whole Inula plant, or the aerial parts thereof, with an organic solvent either by maceration of the plant in the solvent, or by percolation of the solvent through the plant. Furthermore, U.S. Pat. No. 4,254,112 to Debat et al. (hereinafter referred to as "Debat") describes the preparation of extracts of *Inula viscosa* and *Inula graveolens* with whole Inula plants which have been dried and ground, and organic solvents, by using a Soxhlet apparatus for at least 4 hours. The yield of paste obtained was 1.75–4%. U.S. Pat. No. 5,176,913 to Honerlagen et al. (hereinafter referred to as "Honerlagen") describes a process for preparing a partial extract from roots of *Inula helenium* which involves contacting the plant material with an organic solvent, adding a drying agent to the solution to remove the water, removing this drying agent and then distilling the dried organic phase. By contrast, the method of the present invention involves either briefly dipping the leaves and stems of the shoots of *Inula viscosa* or *Inula graveolens* into an organic solvent or shaking the freshly cut or dried and ground leaves and stems of the shoots in an organic solvent for 30 minutes, and then evaporating the solvent to form a paste. Furthermore, the yield of paste obtained by these methods is as much as 30%, in contrast to the low yields known in the literature.

The medicinal properties of Inula extracts in humans are well known. For example, Debat disclosed the antimicrobial activity of extracts of Inula for use in human beings. However, the fungicidal effects of Inula extracts have only been demonstrated on fungi growing in petri dishes or on post-harvest fruits. For example, Qasem et al. (*Phytopathologia Mediterrana* 34:7–14, 1995) demonstrated that the growth of certain fungi in petri dishes was inhibited by aqueous extracts of *Inula viscosa* as well as by dried plant material added directly to the fungal growth media. By contrast, the method of the present invention uses Inula extracts prepared with organic solvents against fungal infections of crop plants themselves.

Clearly, although Inula extracts have been shown to have fungicidal activity in the petri dish, the methods of preparation for these extracts have not been sufficient for large-scale use directly on crop plants. The true effectiveness of these extracts against fungal infections of plants is therefore unknown. Furthermore, there is a clear need for better methods to prepare Inula extracts. Qasem et al. (Ibid, page 13, 1995) concluded: "The diversity in the methodology of extraction and the differences in the results obtained . . . increased the need for developing more efficient, convenient and cheaper methods of extraction to facilitate more extensive utilization of fungicidal extracts, especially if greater quantity of extracts must be prepared for large-scale production".

Furthermore, methods of preparing Inula suspensions are not known in the art, because of technical difficulties with such suspensions. One potential problem with these suspensions is that the Inula powder can fall out of suspension. Furthermore, unless the particle size of the powder is extremely small (less than 50 $\mu$m), particles of the powder can block applicators, such as spray nozzles. Thus, Inula suspensions could not have been previously used for controlling fungal infections in crop plants, for example, because the powder can easily block the spray nozzles used for applying the suspension to the crop plants.

There is thus a widely recognized need for, and it would be highly advantageous to have, a method or methods for preparing extracts and suspensions of plants of the Inula species which would facilitate the large-scale use of these extracts and suspensions, as well as methods for using these extracts and suspensions to control fungal infections in crop plants.

SUMMARY OF THE INVENTION

According to the present invention there is provided a method for preparing an extract of Inula species which comprises (a) contacting shoots of the species with an organic solvent to form a solution and debris; (b) removing the debris from the solution; and (c) evaporating the solution to form a paste.

In a preferred embodiment, the starting material is the leaves and stem of the upper, younger part of the shoots, the upper part of the shoot extending from about 20 to about 40 cm from the tip of the shoot. The flowers are not used. Hereinafter the term "shoot" shall be used to denote the leaves and stem of the shoot of the Inula plant.

Under field conditions in Israel, Inula plants produce four tons of dry shoot material per hectare between April and August, which can result in the production of one ton of Inula extract per hectare.

In a more preferred embodiment, the solvent used is taken from the group which includes, but is not limited to, n-hexane, chloroform, acetone, ethylacetate, diethylether, ethanol, methanol, or their mixtures thereof. These mixtures include, but are not limited to, chloroform and methanol, ethylacetate and methanol, acetone and n-hexane, chloroform and n-hexane, ethylacetate and n-hexane, ethanol and n-hexane, and ethylacetate, methanol and n-hexane.

In another more preferred embodiment, the specific species of the Inula plant which are used are *Inula viscosa* and *Inula graveolens*.

In yet another more preferred embodiment, the paste is dissolved in a carrier. Preferably, the carrier is an organic solvent. Alternatively, the paste is dissolved in a small amount of an organic solvent, and then in water with an additive, such as an appropriate emulsifier or emulsifiers, or an additional appropriate adjuvant or adjuvants. Preferably, the emulsifier is Atlox 4851B ®.

In a still more preferred embodiment, an extract of freshly cut shoots of Inula is prepared by briefly dipping the whole shoots in an organic solvent for from about 10 to about 15 seconds. The organic solvent is taken from the group which includes, but is not limited to, n-hexane, chloroform, acetone, ethylacetate, diethylether or their mixtures thereof. The extraction can be carried out by using a ratio of volume of organic solvent to weight of the shoots of about one liter of organic solvent to from about 300 to about 600 g of freshly cut shoots. After the extraction, the shoots are discarded, the resultant extract is filtered through paper to remove debris from the solution and the solvent is evaporated by either a stream of air in a hood, or under reduced pressure at 37° C. The product thus obtained is a colorless, brown-yellow or yellow paste with no water residues. This paste is then weighed and dissolved in an organic solvent taken from the group which includes, but is not limited to, n-hexane, chloroform, acetone, ethylacetate, diethylether or their mixtures thereof. Alternatively, the paste can be emulsified in water with the aid of an additive, and an appropriate emulsifier or emulsifiers, or an additional appropriate adjuvant or adjuvants.

In a second preferred embodiment, the method of extraction also starts with freshly cut shoots of Inula species. These freshly cut shoots are shaken in an organic solvent for about 30 minutes at 120 rpm at room temperature, in a ratio of volume of the organic solvent to the weight of the shoots of about one liter of the organic solvent to from about 100 to about 300 g of freshly cut shoots, without first homogenizing the shoots. The solvent is taken from the group which includes, but is not limited to, n-hexane, chloroform, acetone, ethylacetate, diethylether, ethanol, methanol or their mixtures thereof. The resultant extract is filtered through paper to remove the debris from the solution, and the solvent is then evaporated by either a stream of air in a hood, or under reduced pressure at 37° C. The product thus obtained is a colorless, brown-yellow, green or yellow paste with no water residues. This paste is then weighed and dissolved in an organic solvent taken from the group which includes, but is not limited to, n-hexane, chloroform, acetone, ethylacetate, diethylether, ethanol, methanol or their mixtures thereof. Alternatively, the paste can be emulsified in water with the aid of an additive and an appropriate emulsifier or emulsifiers, or an additional appropriate adjuvant or adjuvants.

In a third preferred embodiment, the method of extraction is similar to the above second method, except that the starting material is dried and ground Inula shoots. These dried and ground shoots are shaken in an organic solvent for about 30 minutes at 120 rpm at room temperature, in a ratio of volume of organic solvent to weight of dried and ground shoots of about one liter of organic solvent to from about 50 to about 250 g of dried and ground shoots. The solvent is taken from the group which includes, but is not limited to, n-hexane, chloroform, acetone, ethylacetate, diethylether, ethanol, methanol or their mixtures thereof. These mixtures include, but are not limited to, chloroform and methanol, ethylacetate and methanol, acetone and n-hexane, chloroform and n-hexane, ethylacetate and n-hexane, ethanol and n-hexane, and ethylacetate, methanol and n-hexane. The resultant extract is filtered through paper to remove the debris from the solution, and the solvent is then evaporated by either a stream of air in a hood, or under reduced pressure at 37° C. The product thus obtained is a colorless, brown-yellow, green or yellow paste with no water residues. This paste is then weighed and dissolved in an organic solvent taken from the group which includes, but is not limited to, n-hexane, chloroform, acetone, ethylacetate, diethylether, ethanol, methanol or their mixtures thereof. Alternatively, the paste can be emulsified in water with the aid of an additive and an appropriate emulsifier or emulsifiers, or an additional appropriate adjuvant or adjuvants.

According to a different embodiment, a method for preparing a suspension of Inula species includes: (a) drying and grinding shoots of the species to form a powder; (b) mixing the powder with an emulsifier to form a mixture; and (c) suspending the mixture in a solvent to form a suspension. Preferably, the solvent is water and the emulsifier is Atlox 4851B® (calcium alkylaryl sulphonate). Alternatively, the emulsifier can be a mixture of a lignin derivative, Sodium lauryl sulphate and diatomaceous earth. Optionally, the powder can be passed through a metal mesh. Preferably, the metal mesh has a pore size of 50 μm.

According to this invention there is also provided a method for protecting plants against fungal infections, comprising the steps of (a) preparing an extract of Inula species by (i) contacting shoots of the species with an organic solvent to form a solution and debris; (ii) removing the debris from the solution; (iii) evaporating the solution to form a paste; and (iv) dissolving the paste in a carrier to form a fungicidal composition; and (b) applying a fungicidally effective amount of the fungicidal composition to a plant for protecting against fungal infection. The preferred concentration of paste in a carrier used in the method for protecting plants against fungal infections ranges from about 0.01 to about 1 percent by weight of paste per volume of carrier.

Solutions or emulsions containing the Inula extract, or the Inula suspension, are sprayed onto the upper leaf surfaces of various crop plants for the control of fungal plant infections, including but not limited to diseases caused by fungi of the Oomycetes, Ascomycetes, Basidiomycetes and *Fungi imperfecti* classes.

The method of the invention is particularly suitable for use against fungi of the Oomycetes, Ascomycetes, Basidiomycetes and *Fungi imperfecti* classes including but not limited to *Phytophthora infestans, Pseudoperonospora cubensis, Plasmopara viticola, Sphaerotheca fuliginea, Cladosporium cucumerinum, Erysiphe graminis, Uromyces appendiculatus* and *Botrytis cinerea,* and in crops including but not limited to grapevines, tomato, wheat, barley, tobacco, potato, onions, cucurbits, bean or crucifers. It should be noted that according to *Fungicides in Plant Disease Control* (Y. L. Nene and P. N. Thapliyal, International Science Publishers, New York, N.Y., USA, 1993), the effective spectrum of activity of a fungicide encompasses entire classes of fungi. If a fungicide is effective against one member of a class, it usually will be effective against other members of that class. Furthermore, if fungi from the same class infect different plants, the same fungicide will be effective against the disease in all the different plants, since fungicides are disease-specific rather than plant-specific.

DESCRIPTION OF THE PREFERRED EMBODIMENTS

The present invention is of a method for preparing extracts and suspensions of Inula species and of a method for using these extracts and suspensions to protect plants against fungal infections.

The invention is illustrated by the following examples, which describe the preparation and use of Inula extracts and suspensions against fungal infections in plants.

To test the efficacy of these extracts and suspensions, experiments were performed in which plants were sprayed using a fine glass atomizer, with either Inula extract or with pure solvent as a control for the Inula extracts, with either Inula extract and emulsifier or with emulsifier solution as a control for the emulsified Inula extracts, and with either Inula suspension, or with water or emulsifier solution as a control for the Inula suspensions. Treated and control plants were then inoculated with a crop-respective fungal pathogen. After an incubation period the extent of the infection was measured. Unless otherwise stated, percentage protection from the disease due to the treatment with the Inula extract or suspension was calculated as:

% control of the disease =

[1 − (% infection in treated plants/% infection in control plants)] × 100

EXAMPLE 1

Methods of Preparation of Inula Extracts Against Fungal Infections in Plants

Method 1: Briefly Dipping Freshly Cut Shoots in an Organic Solvent

Freshly cut leaves and stems of the upper parts of *Inula viscosa* and *Inula graveolens,* preferably the section extending 20–40 cm from the tip of the shoot, were briefly dipped in an organic solvent for 10–15 seconds. One liter of solvent was used per 300–600 g of shoots. The solvent used was selected from the group including n-hexane, chloroform, acetone, diethylether or ethylacetate. After dipping, the plant material was discarded, the extract was filtered through paper and the solvent was evaporated by a stream of air or under reduced pressure at 37° C. A paste was obtained with no water residues.

The yields of paste obtained are given in Table 1. The yield ranges between 4.50–6.64 g of paste per 100 g of freshly cut shoots, with the exception of n-hexane, which yielded 0.55 g paste per 100 g of freshly cut shoots. To obtain the data in Table 1, 100 g of freshly cut shoots were used in 0.25 liter of solvent.

Method 2: Shaking Freshly Cut Shoots for 30 Minutes

The freshly cut shoots as described in Method 1 above were placed in an organic solvent and shaken for 30 minutes at 120 rpm at room temperature. One liter of solvent was used per 100–300 g of freshly cut shoots. The solvent was selected from the group including n-hexane, chloroform, acetone, ethylacetate, diethylether, ethanol or methanol. Water extraction was performed as a control. After extraction the debris was removed by filtration and the solvent was evaporated as in Method 1 above.

The yields of paste obtained are given in Table 1. Extract processed with water gave the lowest yield, only 0.96 g of paste per 100 g of freshly cut Inula shoots. The second lowest yield was obtained with n-hexane, giving 1.60 g of paste per 100 g of freshly cut shoots. Other solvents yielded 4.00–6.24 g of paste per 100 g of freshly cut shoots. The highest yield, 6.24 g of paste per 100 g of freshly cut shoots, was obtained with ethylacetate. To obtain the data in Table 1, 100 g of shoots were used in 1 liter of solvent.

Method 3: Shaking Dried, Ground Shoots for 30 Minutes

Freshly cut shoots as described in Method 1 were placed under blowing air at room temperature for one day until dry. The water content of these dried shoots was 8–10%, while freshly cut shoots contained 58–60% water. These dried shoots were crushed, placed in an organic solvent or water as a control and then shaken for 30 minutes at 120 rpm at room temperature. The organic solvent was selected from the group including n-hexane, chloroform, acetone, ethylacetate, diethylether, ethanol or methanol, or their mixtures thereof. These mixtures include chloroform and methanol, ethylacetate and methanol, acetone and n-hexane, chloroform and n-hexane, ethylacetate and n-hexane, ethanol and n-hexane in a 1:1 vol/vol ratio, and ethylacetate, methanol and n-hexane in a 1:1:1 vol/vol/vol ratio. One liter of solvent or solvent mixture was used per 50–250 g of dried, ground shoots. After extraction, the plant material was removed by filtration of the solution through paper. The solvent was evaporated as in Method 1 above.

The yields of paste obtained are given in Table 1. The lowest yield was obtained with n-hexane, 3.52 g of paste per 10 g dried, ground shoots. The second lowest yield was obtained with water, 12.8 g of paste per 10 g dried, ground shoots. The other solvents yielded 14.4–36.2 g of paste per 10 g of dried, ground shoots. To obtain the data in Table 1, 10 g of dried and ground shoots were used with 0.1 liter of solvent or solvent mixture.

TABLE 1

Yield of different methods of preparing Inula extracts

| | Dry weight of extract (grams per 100 g starting material) Extraction Procedure | | |
|---|---|---|---|
| Solvent | Freshly cut shoots, dipping for 10 sec* | Freshly cut shoots, shaking for 30 min** | Dried shoots, shaking for 30 min*** |
| Water | — | 0.96 | 12.80 |
| Methanol | — | 4.48 | 29.76 |
| Ethanol | — | 4.96 | 20.80 |
| Acetone | 5.04 | 4.80 | 19.84 |
| Ethylacetate | 4.87 | 6.24 | 22.08 |
| Diethylether | 4.50 | 4.00 | 14.40 |
| Chloroform | 6.64 | 4.64 | 16.00 |
| n-Hexane | 0.55 | 1.60 | 3.52 |
| Chloroform + Methanol | — | — | 30.20 |
| Ethylacetate + Methanol | — | — | 33.80 |
| Acetone + n-Hexane | — | — | 20.70 |
| Ethylacetate + Methanol + n-Hexane | — | — | 36.20 |
| Chloroform + n-Hexane | — | — | 20.00 |
| Ethylacetate + n-Hexane | — | — | 18.40 |
| Ethanol + n-Hexane | — | — | 25.80 |

*100 g freshly cut shoots extracted in 0.25 liter of solvent
**100 g freshly cut shoots extracted in 1 liter of solvent
***10 g dried and ground shoots extracted in 0.1 liter of solvent

EXAMPLE 2

The Fungicidal Effects of Components of Inula Extracts After Separation by Thin-layer Chromatography Inula extracts were prepared according to Method 1, using 100 g of freshly cut shoots of *Inula viscosa* in 0.25 liter of chloroform, acetone, ethylacetate, diethylether or n-hexane. 0.55–6.64 g of paste was obtained. The paste was dissolved in the original solvent to form a 4% solution, percentage by weight.

Extracts were also prepared according to Method 3, using 10 g of dried, ground *Inula viscosa* shoots in 0.1 liter of water, methanol, ethanol, chloroform, acetone, ethylacetate, diethylether or n-hexane. 3.52–29.76 g of paste were obtained. The paste was dissolved in the original solvent to form a 4% solution, percentage by weight.

Twenty microliters (0.02 ml) of each of the solutions were spotted on a silica-gel plate for thin-layer chromatography (TLC). The TLC plates were run in chloroform:methanol 90:10 (v/v) and then developed to determine the number and intensity of components with fungicidal action. Plates were developed either by using iodine vapor ($I_2$) or by overlaying the TLC plate with a conidial suspension of the fungus *Cladosporium cucumerinum* in 1% potato dextrose broth, and then incubating the plate in a moist box at 25° C. for 3 days. In both cases, the $R_f$ value for each spot was measured. The numerical results of the fungicidal activity of the Inula extracts prepared with chloroform according to Method 1 are summarized in Table 2.

Using Method 1, the chloroform extract gave 10 spots with iodine vapor, of which 7 were inhibitory to *C. cucumerinum*. Similar results were seen after using Method 1 with the other solvents, except water and n-hexane. n-Hexane yielded only 3 inhibitory compounds (compounds 7, 8 and 9), which had an $I_2$ staining intensity of ++ and inhibited growth zones of 8–10 mm. Similar results were seen using *I. graveolens*.

TABLE 2

Results of thin-layer chromatography separation and bioassay of the fungicidal properties of Inula extract

| Compound Number | $R_f$ of Compound* | $I_2$ Staining Intensity | Width of Zone of Inhibited Growth of *C. cucumerinum* (mm) |
|---|---|---|---|
| 1 | 0.00 | – | 0 |
| 2 | 0.31 | ++ | 7 |
| 3 | 0.35 | ++ | 0 |
| 4 | 0.37 | ++ | 0 |
| 5 | 0.42 | ++ | 5 |
| 6 | 0.49 | +++ | 11 |
| 7 | 0.53 | ++++ | 15 |
| 8 | 0.64 | ++++ | 10 |
| 9 | 0.72 | ++++ | 15 |
| 10 | 0.81 | + | 3 |

*Note: $R_f$ values may vary ± 10% between experiments

When Method 3 and the solvents acetone, diethylether, chloroform and ethylactate were used, the results obtained were identical to those shown in Table 2 for Method 1 with chloroform. Ethanol and methanol also produced identical results, except that compound 1 had an intensity of + and ++, respectively. Also, compound 1 produced by ethanol showed no inhibition of *C. cucumerinum*. Extracts prepared with n-hexane according to Method 3 produced similar results as extracts prepared according to Method 1: only three inhibitory compounds were produced (compounds 7, 8 and 9). Extracts prepared with water according to Method 3 only produced compounds 1 and 9, with $I_2$ staining intensities of +++ and ±, respectively. Compound 1 showed no inhibitory effect on the growth of *C. cucumerinum*, while compound 9 had a slight effect, with an inhibitory zone of 4 mm. Similar results were seen with *I. graveolens*.

EXAMPLE 3

The Effect of Inula Extracts on Fungal Growth in vitro

Inula extract was prepared according to Method 1, with 100 g of freshly cut shoots of *Inula viscosa* or *Inula graveolens* and 0.5 liter of chloroform. The yield was 7 g of paste, which was dissolved in acetone, and then diluted in acetone to form 0.01–1% solution. Ten μl droplets of solutions in acetone with various concentrations of Inula extract were pipetted into depressions of microscope glass slides, the solvent evaporated instantly, and 10 μl sporangial suspension of the fungus *Phytophthora infestans*, urediospores of *Uromyces appendiculatus* and conidia of *Botrytis cinerea* added. Slides were incubated for 20 hours at 15° C., 20° C. and 25° C., respectively, while sitting on wet filter paper enclosed in petri dishes. The percentage germination of the spores was then evaluated using a microscope. Results are presented in Table 3, using extract of *I. viscosa*. Similar results were seen for *I. graveolens*.

TABLE 3

The effect of Inula extract on zoospore discharge and cytospore germination of *Phytophthora infestans*, urediospore germination of *Uromyces appendiculatus* and spore germination of *Botrytis cinerea*.

| | Concentration of Inula extract (%) | | | |
|---|---|---|---|---|
| | *P. infestans* | | *U. appendiculatus* | *B. cinerea* |
| Inhibition of Fungal Activity (%) | Zoospore Discharge | Cytospore Germination | Urediospore Germination | Conidial Germination |
| 50% Inhibition | 0.075 | 0.05 | 0.03 | 0.1 |
| 100% Inhibition | 0.2 | 0.1 | 0.2 | 0.3 |

The extract was prepared as described in Example 3 and then sprayed, at various concentrations, onto the upper leaf surfaces of 5 week old potato plants. Acetone alone was sprayed as control. Plants were inoculated 1 day later with sporangia of *Phytophthora infestans*, placed in a dew chamber overnight to ensure infection, and then placed in a growth chamber at 20° C. for 7 days. The protection against late blight caused by *P. infestans* is presented in Table 4, using *I. viscosa*. Similar results were seen with *I. graveolens*.

TABLE 4

The protective effect of Inula extract on late blight development in potato

| Concentration of Inula Extract (%) | Blighted Leaf Area (%) | Protection Against Blight (%) |
|---|---|---|
| 0 (acetone control) | 100 | 0 |
| 0.00125 | 86 | 14 |
| 0.0250 | 80 | 20 |

TABLE 4-continued

The protective effect of Inula extract on late blight development in potato

| Concentration of Inula Extract (%) | Blighted Leaf Area (%) | Protection Against Blight (%) |
| --- | --- | --- |
| 0.05 | 60 | 40 |
| 0.1 | 50 | 50 |
| 0.2 | 35 | 65 |
| 0.4 | 5 | 95 |

EXAMPLE 5

The Effect of Inula Extract Against Downy Mildew in Cucumber

The extract was prepared as described in Example 3 and sprayed as described in Example 4 onto the upper leaf surfaces of 3 week old cucumber plants. After one day, the sprayed plants were inoculated with sporangia of *Pseudoperonospora cubensis*, which is the causal agent of downy mildew in cucurbits. Plants were incubated under the same conditions described in Example 4. Results are shown in Table 5, using *I. viscosa*. Similar results were seen with *I. graveolens*, within ±5% of inhibition of disease spread.

TABLE 5

The protective effect of Inula extract against *Pseudoperonospora cubensis* in cucumbers.

| Concentration of Inula Extract (%) | Mildewed Leaf Area (%) | Protection Against Downy Mildew (%) |
| --- | --- | --- |
| 0 (acetone control) | 78 | 6 |
| 0.00125 | 58 | 26 |
| 0.0250 | 45 | 42 |
| 0.05 | 38 | 51 |
| 0.1 | 25 | 68 |
| 0.2 | 13 | 83 |
| 0.4 | 3 | 96 |

EXAMPLE 6

The Effect of Inula Extract Against Powdery Mildew in Cucumber

Cucumber plants were treated in the same manner described in Example 5 except that the plants were inoculated with the fungus *Sphaerotheca fuliginea* which causes powdery mildew disease in cucurbits. Results are presented in Table 6, using *I. viscosa*. Similar results were obtained with *I. graveolens*.

TABLE 6

The protective effect of Inula chloroform extract against powdery mildew caused by *Sphaerotheca fuliginea* in cucumber plants.

| Concentration of Inula Extract (%) | Mildewed Leaf Area (%) | Protection Against Powdery Mildew (%) |
| --- | --- | --- |
| 0 (acetone conttol) | 60 | 0 |
| 0.25 | 35 | 42 |
| 0.5 | 15 | 75 |
| 1.0 | 0 | 100 |

EXAMPLE 7

Effect of Inula Extract Against Gray Mold

This example was carried out with cucumber plants in the same manner described in Example 6 except that younger plants at cotyledonary stage growth were inoculated with conidia of the fungus *Botrytis cinerea*, which causes gray mold. Results are given in Table 7, using *I. viscosa*. Similar results were obtained using *I. graveolens*.

TABLE 7

The protective effect of Inula extract against gray mold caused by *Botrytis cinerea* in cucumber plants.

| Concentration of Inula Extract (%) | Alive Plants (%) |
| --- | --- |
| 0 (acetone control) | 0 |
| 0.25 | 40 |
| 0.5 | 70 |
| 1.0 | 100 |

EXAMPLE 8

Effect of Inula Extract Against Powdery Mildew in Wheat and Barley

The extract was prepared as described in Example 3 and sprayed onto young, 1-leaf stage, wheat or barley plants. Plants were dusted, 1 day later, with conidia of the fungi *Erysiphe graminis* f.sp. *tritici* on wheat, and *E. graminis* f.sp. *hordei* on barley. Both fungi cause powdery mildew disease on their host. Results are shown in Table 8, using *I. viscosa*. Similar results were obtained with *I. graveolens*.

TABLE 8

The protective effect of Inula extract against powdery mildew in wheat and barley.

| Concentration of Inula Extract (%) | Mildewed Leaf Area (%) | | Protection Against Powdery Mildew (%) | |
| --- | --- | --- | --- | --- |
| | Wheat | Barley | Wheat | Barley |
| 0 (acetone control) | 92 | 80 | 0 | 0 |
| 0.05 | 3 | 5 | 97 | 94 |
| 0.1 | 0 | 0 | 100 | 100 |
| 0.2 | 0 | 0 | 100 | 100 |

EXAMPLE 9

Protective Effect of Extracts Prepared by Dipping Freshly Cut Shoots

Inula extracts were prepared according to Method 1, using 100 g of freshly cut Inula shoots and 0.25 liter of either chloroform, acetone, ethylacetate or n-hexane. The paste obtained was dissolved in acetone to form a 0.25 % solution, percent by weight. The various solutions were sprayed on potato, cucumber and wheat plants, which were then inoculated with the appropriate fungal pathogen and incubated for 7 days. Results are shown in Table 9, using *I. viscosa*. Similar results were obtained using *I. graveolens*.

TABLE 9

Protection of crop plants by extracts made according to Method 1.

| Solvent Used for Extraction | Potato Late Blight | Cucumber Downy Mildew | Cucumber Powdery Mildew | Wheat Powdery Mildew |
|---|---|---|---|---|
| Chloroform | 100 | 93 | 90 | 89 |
| Acetone | 94 | 95 | 65 | 96 |
| Ethylacetate | 96 | 98 | 75 | 98 |
| n-Hexane | 96 | 88 | 95 | 100 |

% Control of the Disease

EXAMPLE 10

Protective Effect of Inula Extracts Prepared by Shaking Freshly Cut Shoots

Inula extracts were prepared according to Method 2, using 100 g of freshly cut Inula shoots and 1.0 liter of either water, chloroform, methanol, ethanol, diethylether, acetone or ethylacetate. A sample of the extract was evaporated to dryness and weighed. The remaining extract was sprayed on potato plants, which were then inoculated with *P. infestans* one day later and incubated for 7 days. Results are presented in Table 10, using *I. viscosa*.

TABLE 10

Protection of potato plants against late blight by extracts made according to Method 2.

| Solvent Used for Extraction | Concentration of Paste (%) | Control of Disease (% Inhibition) |
|---|---|---|
| Water | 0.12 | 0 |
| Methanol | 0.56 | 96 |
| Ethanol | 0.62 | 97 |
| Acetone | 0.60 | 94 |
| Ethylacetate | 0.78 | 95 |
| Diethylether | 0.50 | 97 |
| Chloroform | 0.58 | 90 |

EXAMPLE 11

Protective Effect of Inula Extracts Prepared by Shaking Dried, Ground Shoots

Extract of Inula was prepared according to Method 3 with 10 g of dried and ground shoots of *Inula viscosa* in 0.1 liter of water or an organic solvent such as methanol, ethanol, acetone, ethylacetate, diethylether, n-hexane or chloroform. Mixtures of these solvents were prepared, using chloroform and n-hexane, ethylacetate and n-hexane, and ethanol and n-hexane, in a 1:1 vol/vol ratio. A sample of the resultant extract was dried and weighed. The remaining extract was diluted with acetone for the organic solvents, or water for the aqueous extract, so as to obtain a 0.4% solution. The solutions were sprayed on potato, cucumber, bean and wheat plants. Plants sprayed with either water for the aqueous extract or pure acetone for the organic solvents served as controls. Treated and control plants were thereafter inoculated, potato with *Phytophthora infestans,* cucumbers with *Pseudoperonospora cubensis* or with *Botrytis cinerea,* bean with *Uromyces appendiculatus* and wheat with *Erysiphe graminis tritici*. Results are presented in Table 11, for *I. viscosa*. Similar results were obtained using *I. graveolens*.

TABLE 11

Protection against plant diseases by extracts of dried, ground Inula shoots prepared according to Method 3.

| Solvent Used for Extraction | Late Blight in Potato | Downy Mildew in Cucumber | Powdery Mildew in Wheat | Powdery Mildew in Cucumber | Rust in Beans | Gray Mold in Cucumber |
|---|---|---|---|---|---|---|
| Water | 26 | 43 | 45 | 37 | 67 | — |
| Methanol | 89 | 99 | 90 | 75 | 95 | — |
| Ethanol | 94 | 99 | 93 | 95 | 97 | — |
| Ethylacetate | 91 | 91 | 83 | 100 | 100 | — |
| Acetone | 99 | 95 | 93 | 75 | 99 | 100 |
| Chloroform | 83 | 100 | 86 | 70 | 99 | — |
| n-Hexane | 97 | 91 | 93 | 97 | 100 | 85 |
| Diethylether | 96 | 91 | 93 | 95 | 100 | — |
| Chloroform + n-Hexane | 76 | — | 94 | — | — | 100 |
| Ethylacetate + n-Hexane | 82 | — | 94 | — | — | 100 |
| Ethanol + n-Hexane | 72 | — | 89 | — | — | 100 |

% Control of the Disease

EXAMPLE 12

Protective Effect of Inula Extracts Prepared with an Emulsifier

Extract of Inula was prepared according to Method 3 with 10 g of dried and ground shoots of *Inula viscosa* in 0.1 liter of a mixture of organic solvents, including chloroform and methanol, ethylacetate and methanol, acetone and n-hexane, in a 1:1 vol/vol ratio, and ethylacetate, methanol and n-hexane, in a 1:1:1 vol/vol/vol ratio. The resultant pastes were dried and weighed. 15.6 g of Atlox 4851B®, an emulsifier, was dissolved in 100 g of acetone, to form a solution, hereinafter designated as "AA". A combination of the AA solution and water is an example of a carrier for the paste. One gram of paste was dissolved in 3 g of this AA solution and 196 g of water were then added, so as to obtain a 0.5% wt/wt paste emulsion in water. A control solution was prepared by adding 3 g of the AA solution to 197 g of water, so as to obtain a 1.5% wt/wt solution.

The paste emulsion was sprayed at full strength (0.5% paste emulsion, wt/wt) onto the upper leaf surfaces of 5 week old potato plants, 3 week old cucumber plants, and 1-leaf stage wheat plants, and at half strength (0.25% paste emulsion, wt/wt) onto the lower leaf surfaces of 15-leaf stage grape plants of the cultivar Shardonet. Plants sprayed either with water or with the control solution served as controls. Potato, cucumber and wheat plants were sprayed with the full strength control solution (1.5%, wt/wt) and grape plants were sprayed with the half strength control solution (0.75%, wt/wt). One day later, treated and control plants were inoculated, potato with *Phytophthora infestans,* cucumbers with *Pseudoperonospora cubensis,* grape plants with *Plasmopara viticola* and wheat with *Erysiphe graminis tritici*. The inoculated potato, cucumber and grape plants were placed in dew chamber overnight to ensure infection, and were then, along with the wheat plants, placed in a growth chamber at 20° C. for 7 days. One week after inoculation, the grape plants were placed in a dew chamber in the dark at 18° C. for 20 hours to induce sporulation of *Plasmopara viticola*.

Results are presented in Table 12 for *I. viscosa* as the control of the disease relative to the control solution, because the control solution alone had an inhibitory effect on fungal infection. Such an inhibitory effect by emulsifiers alone is well known in the literature. The strength of both the Inula and control solutions was halved for spraying onto grape plants because both solutions had a very strong inhibitory effect against fungal infection. In fact, the full strength Inula solution had a complete inhibitory effect against *P. viticola*.

TABLE 12

Protection of crop plants by Inula extracts made with an emulsifier.

| Solvent | % Control of the Disease | | | |
|---|---|---|---|---|
| Mixtures Used for Extraction | Potato Late Blight | Cucumber Downy Mildew | Grapes Downy Mildew | Wheat Powdery Mildew |
| Chloroform + Methanol | 86 | 33 | 62 | 74 |
| Ethylacetate + Methanol | 62 | 50 | 38 | 72 |
| Acetone + n-Hexane | 95 | 66 | 87 | 92 |
| Ethylacetate + Methanol + n-Hexane | 63 | 50 | 38 | 50 |

EXAMPLE 13

Methods of Preparation of Inula Suspensions Against Fungal Infections in Plants

Method 4: Preparing an Inula Suspension with Atlox 4851B ®

Freshly cut shoots were dried as described in Method 3. The dried plant material was ground in a Waring blender at high speed for 30 minutes and then screened through a metal mesh with 50 µm pore size, producing a powder. A suspension of the powder was prepared according to the following procedure. One gram of Inula powder with a particle size less than or equal to 50 µm was mixed with 0.5 g of Atlox 4851B®, and 98.5 g of water was then added. The mixture was stirred at high speed for 10 minutes, producing a powder suspension. As a control, a solution of 0.5 g of Atlox 4851B® and 99.5 g of water was prepared. Atlox 4851B® is the registered trademark of ICI, United Kingdom. Chemically, Atlox 4851B® is a non-ionic blend of calcium alkylarylsulphonate and is an emulsifier.

The resulting powder suspension was sprayed onto the foliage of potato, cucumber and barley plants. Plants sprayed with either water or 0.5 g of Atlox 4851B® in water alone served as controls. One day after being sprayed, plants were inoculated with their respective fungal pathogens: late blight for potato, downy mildew for cucumber and powdery mildew for barley. The area of diseased leaf was estimated one week later. Results are presented in Table 13 below.

TABLE 13

Efficacy of Inula powder suspension against fungal infection

| | Leaf Area Infected (%) | | |
|---|---|---|---|
| Suspension | Late Blight in Potato | Downy Mildew in Cucumber | Powdery Mildew in Barley |
| Water Control | 100 | 69 | 75 |
| Atlox 4851B ® Control | 100 | 38 | 50 |
| Inula Suspension | 18 | 3 | 9 |

Clearly, the Inula powder suspension had a strongly inhibitory effect on fungal growth. Relative to the Atlox 4851B ® control, the Inula powder suspension provided 82% protection against late blight infection in potato, 92% protection against downy mildew in cucumber and 82% protection against powdery mildew in barley.

Method 5: Preparing an Inula Suspension with Wettable Powder

Freshly cut shoots were dried as described in Method 3. The dried plant material was ground in a Waring blender at high speed for 30 minutes and then screened through a metal mesh with 50 µm pore size, producing a powder. The powder was then milled for ten minutes in a mortar and pestle, and screened through a metal mesh with 50 µm pore size again. One gram of Inula powder, of a particle size less than or equal to 50 µm, was mixed with 0.5 g of wettable powder (see below for the formulation of wettable powder). The mixture was again milled for 10 minutes with a mortar and pestle. The mixture was passed again through a 50 µm metal mesh and suspended in 98.5 g of water. As a control, a second suspension was prepared of 0.5 g of wettable powder alone in 99.5 g of water.

Wettable powder was prepared by mixing 64 g of Vercoryl-S (Kaolin), 5 g of Polyfon-O (lignin derivative), 3 g of Sodium lauryl sulphate and 2 of Celite-400 (diatomaceous earth). The mixture was then milled for 10 minutes with a mortar and pestle. The resulting powder was then passed through a 50 µm metal mesh.

The resulting powder suspension was sprayed onto the foliage of potato, cucumber and barley plants. Plants sprayed with either water or 0.5 g of wettable powder in water alone served as controls. One day after being sprayed, plants were inoculated with their respective fungal pathogens: late light for potato, downy mildew for cucumber and powdery mildew for barley. The area of diseased leaf was estimated one week later. Results are presented in Table 14 below.

TABLE 14

Efficacy of Inula powder suspension against fungal infection

| | Leaf Area Infected (%) | | |
|---|---|---|---|
| Suspension | Late Blight in Potato | Powdery Mildew in Wheat | Powdery Mildew in Barley |
| Water Control | 90 | 75 | 75 |
| Wettable Powder Control | 72 | 75 | 75 |
| Inula Suspension | 30 | 20 | 18 |

Clearly, the Inula powder suspension had a strongly inhibitory effect on fungal growth. Relative to the wettable powder control, the Inula powder suspension provided 58% protection against late blight infection in potato, 76% protection against powdery mildew in barley and 73% protection against powdery mildew in wheat.

While the invention has been described with respect to a limited number of embodiments, it will be appreciated that many variations, modifications and other applications of the invention may be made.

What is claimed is:

1. A method for preparing a suspension of Inula species which comprises:
    (a) drying and grinding shoots of the species to form a powder;
    (b) mixing said powder with an emulsifier to form a mixture; and
    (c) suspending said mixture in a solvent to form a suspension.

2. The method according to claim 1, wherein said solvent is water.

3. The method according to claim 1, wherein said emulsifier is calcium alkylaryl sulphonate.

4. The method according to claim 1, wherein said emulsifier is a mixture of a lignin derivative, Sodium lauryl sulphate and diatomaceous earth.

5. The method according to claim 1, further comprising the step of passing said powder through a metal mesh.

6. The method according to claim 5, wherein said metal mesh has a pore size of 50 microns.

7. A method for protecting plants against fungal infections, comprising the steps of:
    (a) preparing a suspension of Inula species by:
        (i) drying and grinding shoots of the species to form a powder;
        (ii) mixing said powder with an emulsifier to form a mixture; and
        (iii) suspending said mixture in a solvent; and
    (b) applying a fungicidally effective amount of said suspension to a plant for protecting against fungal infection.

8. The method according to claim 7, wherein said plant is selected from the group consisting of grapevines, cucurbits, tomato, wheat, barley, onion, tobacco, crucifers, bean and potato.

9. The method according to claim 7, wherein said fungal infection is caused by phytopathogenic fungi of a class selected from the group consisting of Oomycetes, Ascomycetes, Basidiomycetes and *Fungi imperfecti*.

10. The method according to claim 9, wherein said flngal infection is caused by a fungus selected from the group consisting of *Cladosporium cucumerinum, Phytophthora infestans, Botrytis cinerea, Pseudoperonospora cubensis, Sphaerotheca fuliginea, Plasmopara viticola, Uromyces appendiculatus* and *Erysiphe graminis*.

11. A fungicidal mixture for plants comprising:
    a powder comprising ground plant material of the species Inula;
    a solvent comprising water and an emulsifier; said powder being suspended in said solvent.

12. A mixture as in claim 11, wherein said emulsifier is a nonionic emulsifier.

13. A mixture as in claim 12, wherein said nonionic emulsifier comprises calcium alkylaryl sulfonate.

14. A mixture as in claim 11, wherein said emulsifier comprises a mixture of a lignin derivative, sodium lauryl sulphate, kaolin and diatomaceous earth.

15. A mixture as in claim 11, wherein said powder has a particle size of 50 microns or less.

16. A mixture as in claim 11, wherein said powder comprises, by weight, 1% of said mixture.

* * * * *